United States Patent
Jung et al.

(10) Patent No.: US 9,943,674 B2
(45) Date of Patent: Apr. 17, 2018

(54) MICROSTRUCTURE-BASED DRUG DELIVERY SYSTEM COMPRISING MICROPOROUS STRUCTURE

(71) Applicant: JUVIC INC., Seoul (KR)

(72) Inventors: Hyung Il Jung, Seoul (KR); Hui Suk Yang, Gyeonggi-do (KR)

(73) Assignee: JUVIC INC., Seoul (KR)

( * ) Notice: Subject to any disclaimer, the term of this patent is extended or adjusted under 35 U.S.C. 154(b) by 0 days.

(21) Appl. No.: 14/622,716

(22) Filed: Feb. 13, 2015

(65) Prior Publication Data

US 2015/0328443 A1    Nov. 19, 2015

(30) Foreign Application Priority Data

Feb. 14, 2014    (KR) .................. 10-2014-0017346
Feb. 14, 2014    (KR) .................. 10-2014-0017348

(51) Int. Cl.
| | | |
|---|---|---|
| *A61M 37/00* | (2006.01) | |
| *A61K 9/70* | (2006.01) | |
| *A61K 9/00* | (2006.01) | |
| *B29C 41/12* | (2006.01) | |
| *B29C 41/36* | (2006.01) | |
| *A61K 9/08* | (2006.01) | |
| *A61K 47/36* | (2006.01) | |
| *B29L 31/00* | (2006.01) | |

(52) U.S. Cl.
CPC ....... *A61M 37/0015* (2013.01); *A61K 9/0021* (2013.01); *A61K 9/0097* (2013.01); *A61K 9/08* (2013.01); *A61K 9/703* (2013.01); *A61K 47/36* (2013.01); *B29C 41/12* (2013.01); *B29C 41/36* (2013.01); *A61M 2037/0046* (2013.01); *A61M 2037/0053* (2013.01); *A61M 2037/0061* (2013.01); *B29L 2031/756* (2013.01); *B29L 2031/7544* (2013.01)

(58) Field of Classification Search
None
See application file for complete search history.

(56) References Cited

U.S. PATENT DOCUMENTS

| | | | | |
|---|---|---|---|---|
| 2002/0082543 | A1* | 6/2002 | Park ................... | A61B 5/1411 604/21 |
| 2011/0045041 | A1* | 2/2011 | Gdalubovic-Liakopoulos | A61K 8/0208 424/401 |

FOREIGN PATENT DOCUMENTS

WO    WO 2013188884 A1 * 12/2013 ............. A61B 17/08

* cited by examiner

*Primary Examiner* — Mina Haghighatian
*Assistant Examiner* — Frank Choi
(74) *Attorney, Agent, or Firm* — Harness, Dickey & Pierce, P.L.C.

(57) ABSTRACT

Disclosed are a microstructure-based drug delivery system comprising a microporous structure and a method for manufacturing the same, and more specifically, a detachable microstructure-based drug delivery system using a microporous structure layer and a method for manufacturing the same, thereby skipping a drying step which is essential for the manufacturing process of the existing biodegradable microneedle, and solving the problem in that the hardness of the microneedle is reduced when the microneedle contains drugs, failing to penetrate the skin. Here, the microstructure is implantable in the body through the insertion into the body and detachment from the microporous structure, and the detachable microstructure can be applied to wrinkled (skin movement) and corrugated parts through a detachment function thereof.

14 Claims, 25 Drawing Sheets

MICROSTRUCTURE-BASED DRUG DELIVERY SYSTEM COMPRISING MICROPOROUS STRUCTURE

CROSS-REFERENCE TO RELATED APPLICATION

This application claims priority to and the benefit of Korean Patent Application Nos. 10-2014-0017346, filed on Feb. 14, 2014 and 10-2014-0017348, filed on Feb. 14, 2014, the disclosure of which is incorporated herein by reference in its entirety.

FIELD

The present invention relates to a microstructure-based drug delivery system comprising a microporous structure and a method for manufacturing the same, and more particularly, to a detachable microstructure-based drug delivery system using a microporous structure layer and to a method for manufacturing the same.

BACKGROUND

Through the present, several techniques have been developed to deliver drugs into the body. Of these, the transdermal delivery of drugs employs injections, ointments, patches, or the like. Injections produce prompt drug effects since a needle is inserted into the body to delivery drugs. Injections are an effective way to deliver drugs due to the delivery of drugs into tissues in the body, such as blood or muscles, and thus are used in various fields. However, the injection causes strong irritation and wounds to the skin, which are accompanied by pain. Moreover, the wounds may bring about further infection, and injections can only be given by experts.

Microneedles are drug delivery systems which are designed in order to solve the above problems. Drugs are delivered into the body through only minimum invasion using microneedles.

Of these, as for a biodegradable microneedle, a microneedle composed of a polymeric material is disposed on a patch, and attached to the skin together with the patch. After the patch is attached, the polymeric material is dissolved through a reaction with body water at body temperature, and here, drugs in the polymeric material are released.

However, this biodegradable microneedle is attached onto the skin in a patch type until the whole polymeric material is dissolved and the loaded drugs are all delivered. Thus, the time of application of the patch inhibits the activity of a user and causes a continuous feeling of irritation. Due to these, timing of application of the biodegradable microneedle is recognized as a limitation, and thus there is a need for a technology to overcome this.

Moreover, the limitation of the timing of application of the patch also causes a limitation of the drug deliverable time of the biodegradable microneedle. While normal drugs need to be continuously delivered into the body at a predetermined quantity, the biodegradable polymeric material has difficulty in drug delivery control after the whole biodegradable polymeric material is dissolved. Thus, the biodegradable microneedle patch is required to be continuously applied. Accordingly, the development of a technology of drug release control through implantation of the biodegradable microneedle is urgently needed.

In addition, in cases where the biodegradable microneedle using a patch is applied to the skin, it is difficult to deliver drugs into wrinkled or corrugated skin. In cases of the wrinkled human skin, the motion of the human body causes movement of the patch, resulting in the detachment of the biodegradable microneedle from the skin, and thus it is impossible to deliver drugs effectively. Also in cases of the corrugated human skin, the biodegradable microneedle cannot completely invade when the patch is applied, due to elasticity of the patch itself.

Meanwhile, the biodegradable microneedle is manufactured by a fine molding method, a drawing method, or a blowing method. All of the above methods for manufacturing the biodegradable microneedle employ mixing a biodegradable polymeric material and drugs. Basically, the biodegradable microneedle is manufactured by preparing a viscous solution in which a biodegradable polymeric material and drugs are mixed, molding a microneedle from the viscous solution, and solidifying the molded material to have a shape and hardness of the microneedle.

Therefore, a solution form in which all the drugs are mixed with the biodegradable polymeric material is used for molding. However, this brings about physical and chemical interactions between the polymeric material and the drugs, causing the degradation in drug activity and the loss of stability.

Additionally, there is a limitation in the kind of drug that can be loaded due to the use of solvent. For example, a hydrophobic drug cannot be used to prepare a solution since it is not mixed with a hydrophilic polymeric material that is mostly used, and thus it is impossible to mold a biodegradable microneedle. Due to this, the biodegradable microneedle, which is manufactured based on a hydrophilic polymeric material for dissolution in the body, has a limitation of not loading a hydrophobic drug.

In addition, the manufacturing process of the biodegradable microneedle necessarily involves a drying step of solidifying a solution to allow the microneedle to have a shape and hardness.

The drying step causes the destruction of the drug structure. The moisture contained in the drug is lost during the drying step, and the drug loses a hydrogen bond with a water molecule, which maintains the drug structure. This causes the destabilization of the drug and the destruction of the drug structure. Also, the drying induces the structural change in the polymeric material, and this change also influences the destabilization of the drug structure.

Due to the above limitations, the existing methods for manufacturing a biodegradable microneedle have a limitation in the kind of loadable drug and the maintenance of drug stability.

Further, when a solution is prepared by mixing a biodegradable polymeric material and drugs, the biodegradable microneedle fails to have sufficient hardness in cases where a predetermined quantity or more of drug is loaded. In those cases, the biodegradable microneedle has difficulty in delivering a predetermined quantity or more of drug.

As described above, the drug delivery techniques have been developed recently, but there are still limitations in delivering insoluble drugs, delivering unstable drugs, storage and distribution, and the like. Accordingly, there is a need for a technology to overcome these limitations, and many studies are being conducted in the corresponding fields.

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

SUMMARY

The present inventors have endeavored to solve the above-described problems in the prior art. As a result, the present inventors have developed a method, based fundamentally on a microstructure, of loading a drug to be delivered in a microporous structure and/or a microstructure. The manufactured microstructure-based drug delivery system can skip a drying step which is essential for the manufacturing process of the existing biodegradable microneedle, does not require the patch to be applied for a long time since it is inserted into the body and then detached therefrom, and can control the drug release through the control of dissolution characteristics in the body, thereby eventually improving efficiency and convenience in the drug delivery by the microstructure. Further, the present inventors manufactured a detachable microstructure which can efficiently deliver the drug into a wrinkled or corrugated part of the body through insertion-detachment-implantation.

Accordingly, an aspect of the present invention is to provide a method for manufacturing a microstructure-based drug delivery system using a microporous structure.

Another aspect of the present invention is to provide a microstructure-based drug delivery system comprising a microporous structure.

Other purposes and advantages of the present disclosure will become clarified by the following detailed description of the invention, claims, and drawings.

In order to accomplish one or more of the above aspects, there is provided a method for manufacturing a microstructure-based drug delivery system using a microporous structure, the method including: (a) forming a microporous structure layer; (b) forming a microstructure on the microporous structure layer; and (c) loading a liquid-phase or solid-phase drug in the microporous structure layer after step (a) or (b) if the drug is loaded in the microporous structure layer, or performing step (b) using a viscous composition containing a liquid-phase or solid-phase drug if the drug is loaded in the microstructure, wherein at least one of the microporous structure layer and the microstructure contains the drug, and the microstructure contains or does not contain the liquid-phase or solid-phase drug if the drug is loaded in the microporous structure layer.

BRIEF DESCRIPTION OF THE DRAWINGS

The above and other objects, features and advantages of the present invention will be more apparent from the following detailed description taken in conjunction with the accompanying drawings, in which:

FIG. 2A shows a surface observation result of a microporous structure formed by electrospinning a 15% polyvinyl alcohol (PVA) solution (×50,000 magnification). FIG. 2B shows a surface observation result of a microporous structure formed by electrospinning an 8% polyvinylpyrrolidone (PVP) solution (×7,000 magnification). FIG. 2C shows a surface observation result of a microporous structure formed by electrospinning a 5% polyethylene oxide (PEO) solution (×7,000 magnification). FIG. 2D shows a surface observation result of a microporous structure formed by electrospinning a 15% poly(lactic-co-glycolic) acid (PLGA) solution. FIG. 2E shows a surface observation result of a microporous structure formed by electrospinning an 11% polyurethane (PU) solution (×7,000 magnification). FIG. 2F shows a surface observation result of a microporous structure formed by electrospinning a 10% polycaprolactone (PCL) solution (×50,000 magnification).

In FIG. 3, the left panel shows an image obtained by magnifying a surface of the microporous structure at a magnification of ×85, and the right panel shows an image obtained by magnifying the same at a magnification of ×1000, indicating the formation of micropores.

In FIG. 5A, when a microneedle formed on the convex protrusion of the substrate is inserted into the skin, the microporous structure layer receives force, and thus a weak area of the microporous structure layer is broken, and eventually, the microneedle is detached from the entire structure. FIG. 5B shows that the microporous structure layer was formed on the substrate patterned to have convex protrusions, and a weak area of the microporous structure layer was inclined from the protrusion of the substrate to the bottom of the substrate. In FIG. 5C, panels (a) to (d) show observation results at magnifications of (a) ×20, (b) ×40, (c) ×10, and (d) ×40.

FIG. 10B shows the microporous structure after the microneedles were detached.

The drug loading characteristics and the drug release characteristics of the drug delivery system can be controlled using various structures of supports (substrates).

Figure 16:
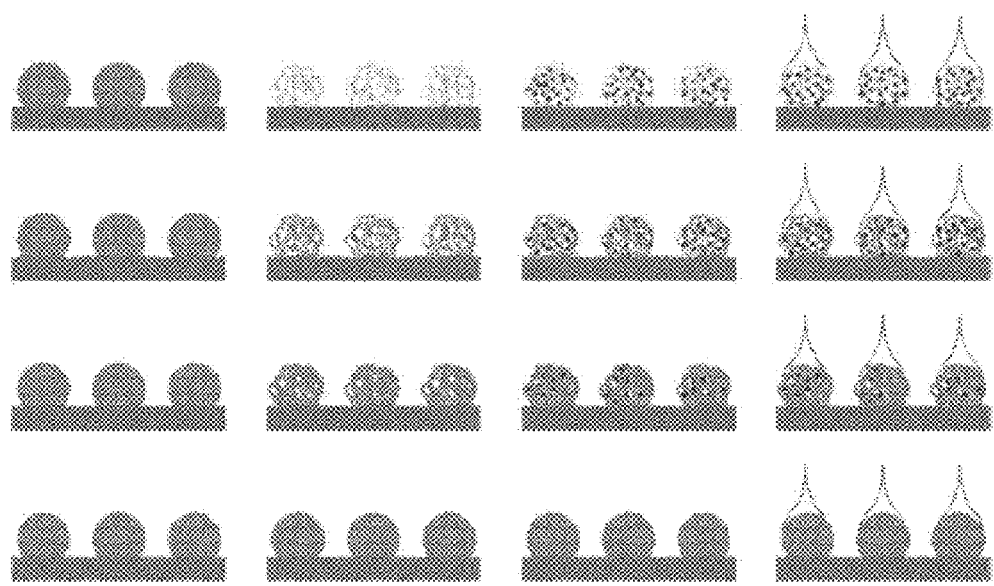

FIG. 16 illustrates that the quantity of drug loaded is controlled according to the porosity of the microporous structure.

Figure 17:
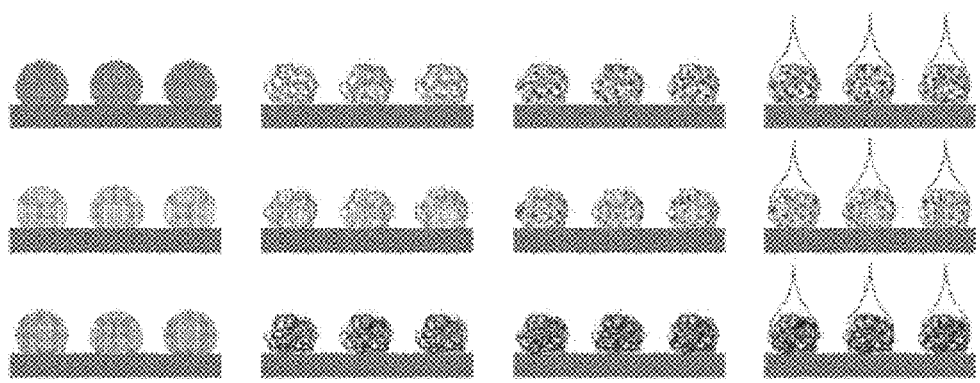

FIG. 17 shows embodiments in which the microstructure-based drug delivery system was manufactured by diversifying the materials constituting the microporous structure.

Figure 18A:
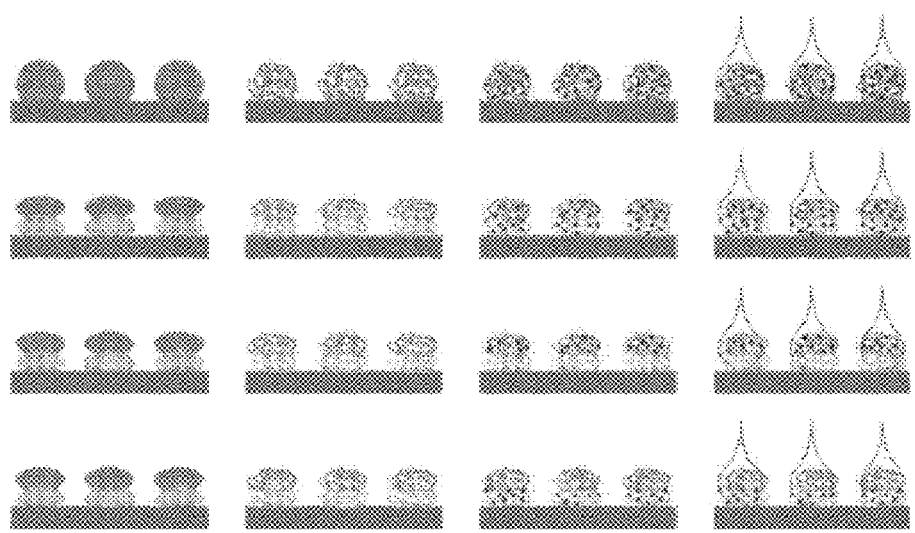

FIG. 18A illustrates multi-layered microporous structures, and the control of drug loading characteristics according to the multi-layered microporous structure. In each of the multi-layered microporous structures, respective layers may be the same or different. The drug loading characteristics can be controlled by controlling physical, chemical, and electrical features of the respective layers.

Figure 18B:
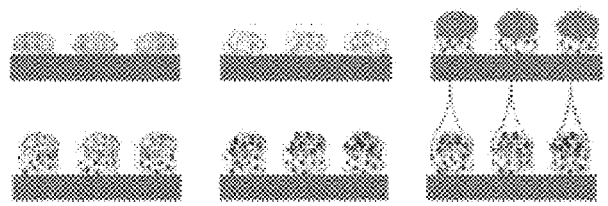

FIG. 18B illustrates multi-layered microporous structures, and the control of drug loading sequence according to the multi-layered microporous structure. In each of the multi-layered microporous structure, different kinds of drugs may be sequentially loaded in the layers, respectively.

Figure 19:
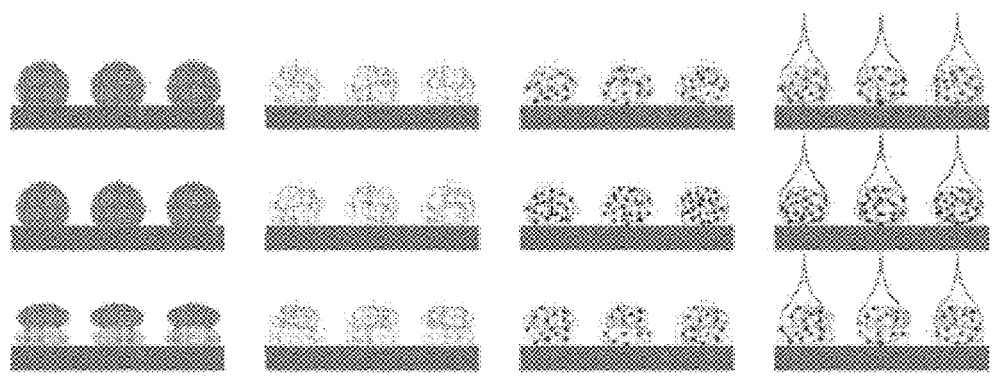

FIG. 19 shows embodiments the diversification of the drug loading in the drug delivery system of the present invention. The same or two or more different drugs may be loaded in one microporous structure. In addition, different kinds of drugs may be loaded in respective layers of the multi-layered microporous structure, using characteristics of the microporous structure and the drugs. The different kinds of drugs may be loaded sequentially or simultaneously.

DETAILED DESCRIPTION

The present inventors have endeavored to solve the above-described problems of the prior art. As a result, the present inventors have developed a method of, fundamentally based on a microstructure, loading a drug to be delivered in a microporous structure and/or a microstructure. The manufactured microstructure-based drug delivery system can skip a drying step which is essential for the manufacturing process of the existing biodegradable microneedle, does not require the patch to be applied for a long time since it is inserted into the body and then detached therefrom, and can control the drug release through the control of dissolution characteristics in the body, thereby eventually improving efficiency and convenience in the drug delivery by the microstructure. Further, the present inventors manufactured a detachable microstructure which can efficiently deliver the drug into a wrinkled or corrugated part of the body through insertion-detachment-implantation.

The method of the present invention will be described by steps in detail as follows.

Step (a): Forming of Microporous Structure Layer

The present invention is characterized in that a microstructure is formed on a microporous structure layer such that the microstructure can be easily detached. The microporous structure layer used herein has a structure of allowing the microstructure to be detached.

According to an embodiment, the microporous structure layer may be formed on a substrate to support the microporous structure layer. The substrate may be manufactured by using various materials such as polymers, organic chemical materials, metals, ceramics and semiconductors. Given that the microstructure of this invention is mainly applied to the skin, the substrate may serve as a backing of patches.

The formation of the microporous structure layer may be undertaken by various processes. For example, a freeze-drying method (Sundararajan V et al., Porous chitosan scaffolds for tissue engineering, Biomaterials, 20(12):1133-1142 (1999)), an electrospinning method (Travis J. Sill et. al., Electrospinning: Applications in drug delivery and tissue engineering, Biomaterials 29:1989-2006 (2008)) and a solvent-removal method (Chun-Jen LIAO et al., Fabrication of porous biodegradable polymer scaffolds using a solvent merging-particulate leaching method, Journal of Biomedical Materials Research, 59(4):676-681 (2002)) may be applied to the formation of the microporous structure layer.

As for the freeze-drying, a microporous structure layer may be formed by, for example, freeze-drying a polymer solution at −20° C. to −150° C. for 30 minutes to 10 hours.

Meanwhile, a polymeric fiber prepared by electrospinning forms a porous structure having superior pore interconnectivity (Travis J. Sill et. al., Electrospinning: Applications in drug delivery and tissue engineering, Biomaterials 29:1989-2006 (2008)). In cases where the microporous structure layer is formed by electrospinning, the microporous structure layer may be formed by, for example, spinning a polymer solution injected in an injection member through a spinning nozzle under a predetermined voltage using an injection pump. In such a case, the applied voltage is not particularly limited, and is for example 1-30 kV, more specifically, 5-20 kV, and most specifically, 9-15 kV.

As for the solvent removal, a microporous structure layer may be formed by, for example, dissolving a polymeric material in an organic solvent, dissolving salt particles in the polymer solution, molding the mixture through a case (template) with a particular shape, and then removing particles by an aqueous solution.

The formed microporous structure layer is a structure having pores with a size of several tens of nanometers to several hundreds of micrometers, and more specifically, several hundreds of nanometers to several tens of micrometers.

Figure 1:
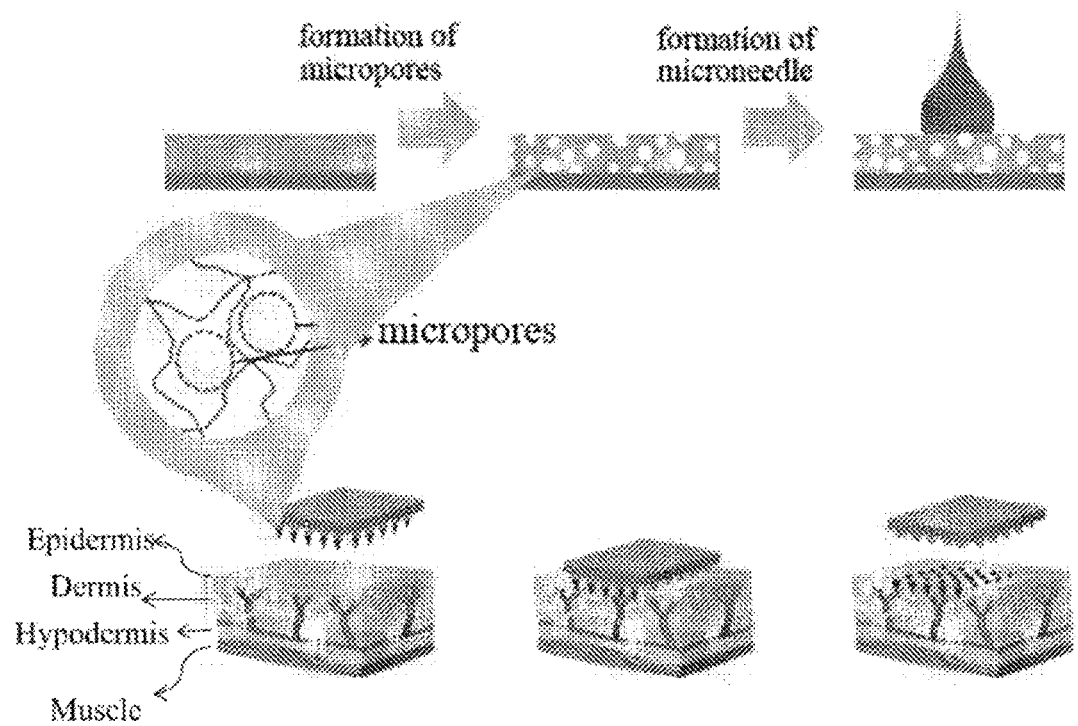
FIG. 1 is a diagram showing the manufacture of a microstructure-based drug delivery system of the present invention, an application thereof, and a detachment function thereof.

A microstructure is combined on such a microporous structure layer. Thus, the microporous structure layer serves as a support of the microstructure. The microporous structure layer as a support is weakly combined with the microstructure and easily broken by physical force when compared with a layer having no micropores. Eventually, the microstructure is detached from the microporous structure layer by the force applied when the microstructure is applied (to, e.g., the skin). Through this performance principle, the microstructure of the present invention can serve as a detachable microstructure (see FIG. 1).

The microporous structure layer may be formed using a polymer solution. Examples of a polymer usable in the formation of the microporous structure layer include a biocompatible material or a biodegradable material used in the formation of the microstructure, as described below.

According to an embodiment of the present invention, the microporous structure layer is formed using a polymer solution, and the size and frequency of micropores of the microporous structure layer are controlled by controlling the kind, molecular weight, concentration, or a combination thereof of a polymer in the polymer solution (see FIGS. 2A to 2F and 3).

According to an embodiment of the present invention, the microporous structure layer is formed by electrospinning, and the size and frequency of micropores of the microporous structure layer are controlled by controlling the thickness, diameter, density, or a combination thereof of polymeric fiber (see FIGS. 2A to 2F). If the size and frequency of the micropores are large, the microstructure is detached by a less weak force.

Figure 4:
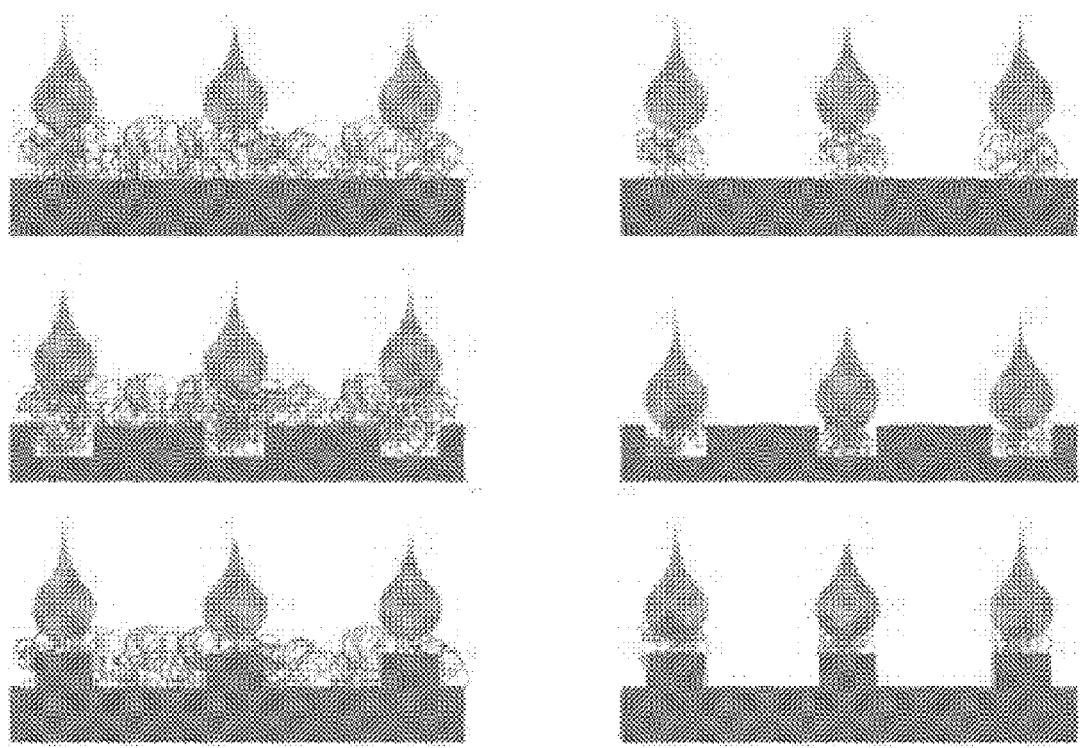
FIG. 4 illustrates embodiments of the present invention with respect to the formation of the microporous structure on a substrate (a support). The embodiments show that the patterns of the microporous structure and the substrate were diversified. The microporous structure may be formed to have a predetermined pattern. In addition, the detaching function of the microstructure may be diversified by controlling the pattern of the substrate and the pattern of the microporous structure.
Figure 5A:
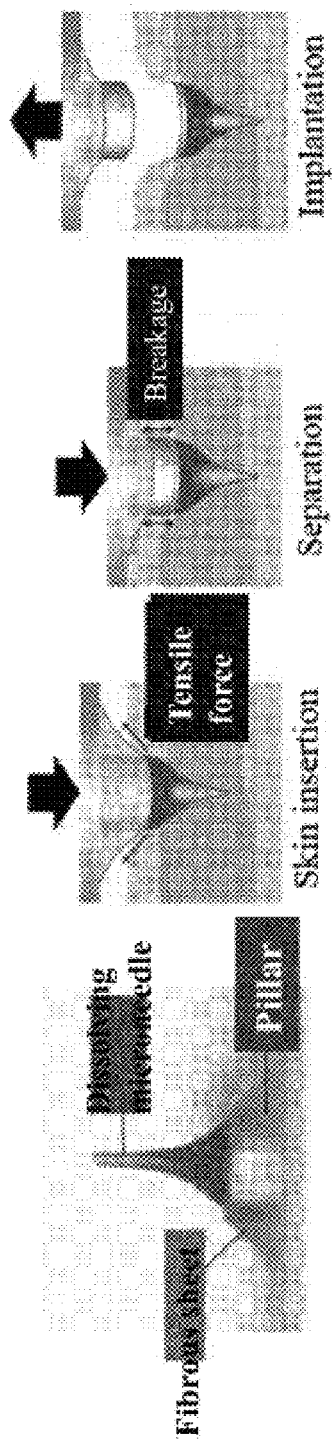
FIGS. 5A to 5C illustrates an embodiment of the present invention with respect to the formation of the microporous structure on a pillar-shaped support (support having a convex portion) using electrospinning.
Figure 5B:
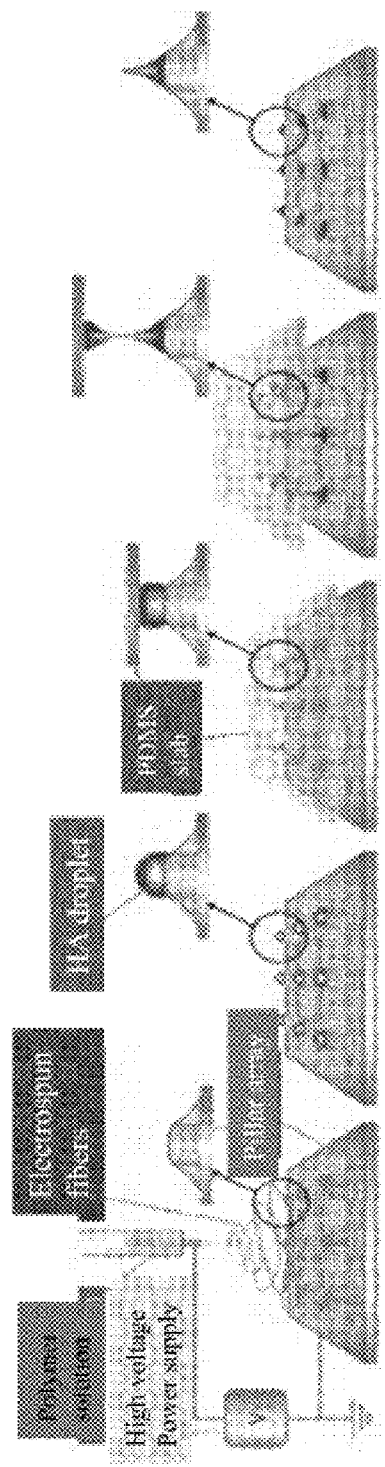
Figure 5C:
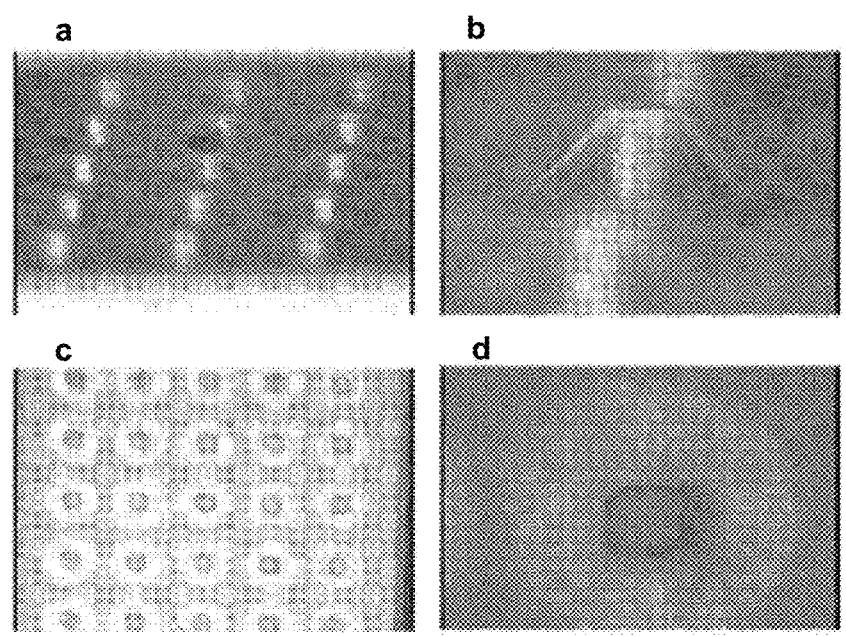
Figure 5D:
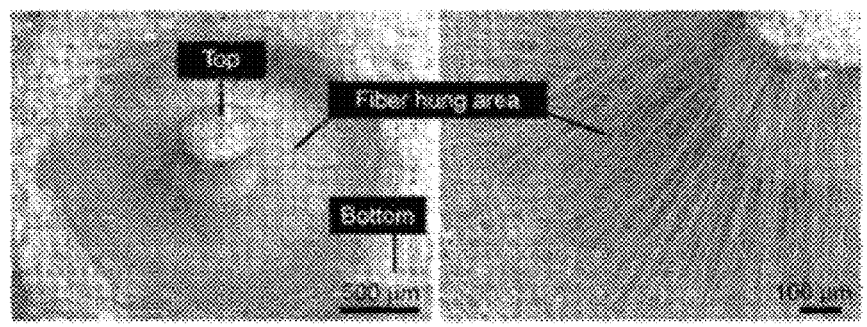
FIG. 5D shows field emission scanning electron microscopy (FESEM) images of FIG. 5C. Lower images of FIG. 5D, 100, 300, and 500 µm indicate heights at different region of the pillar.
Figure 5D:
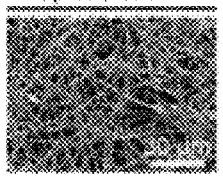
Figure 5D:
Figure 5E:
FIG. 5E shows images illustrating that a hyaluronic add pillar was formed using centrifugal force. The right image is a magnification of the left image.
Figure 5F:
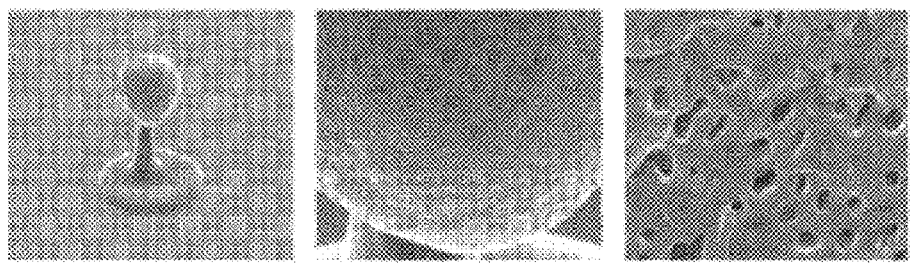
FIG. 5F shows images illustrating that a microporous structure was formed on the hyaluronic acid pillar by freeze-drying. The middle and right images are magnifications of the left image, and show a plurality of micropores.
Figure 5G:
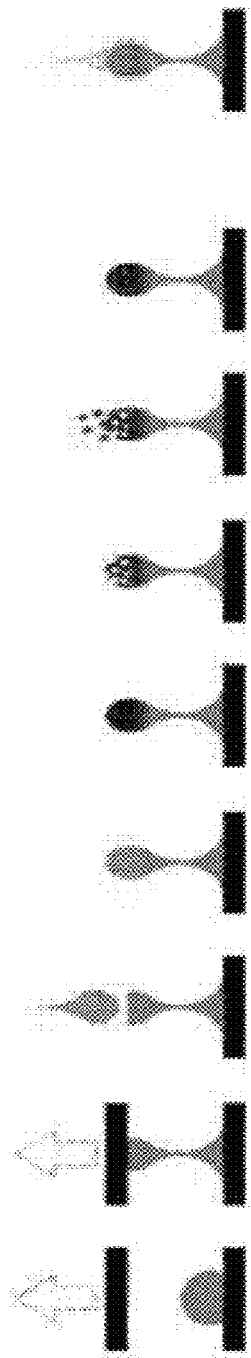
FIG. 5G shows an embodiment of the present invention with respect to the manufacture of the microstructure-based drug delivery system. From the leftmost panel, the panels show forming a pillar support using centrifugal force, discharging a polymer viscous composition, forming a microporous structure using freeze-drying, loading a solid-phase drug in the microporous structure, and forming a microneedle on the microporous structure.
Figure 5H:
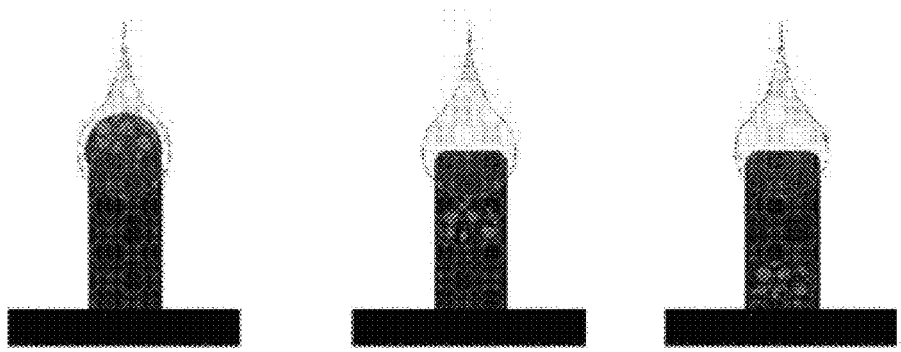
FIG. 5H shows images illustrating that, when a pillar is used as a support, a microporous structure layer may be formed in an upper portion, a middle portion, or a lower portion of the pillar.
Figure 6:
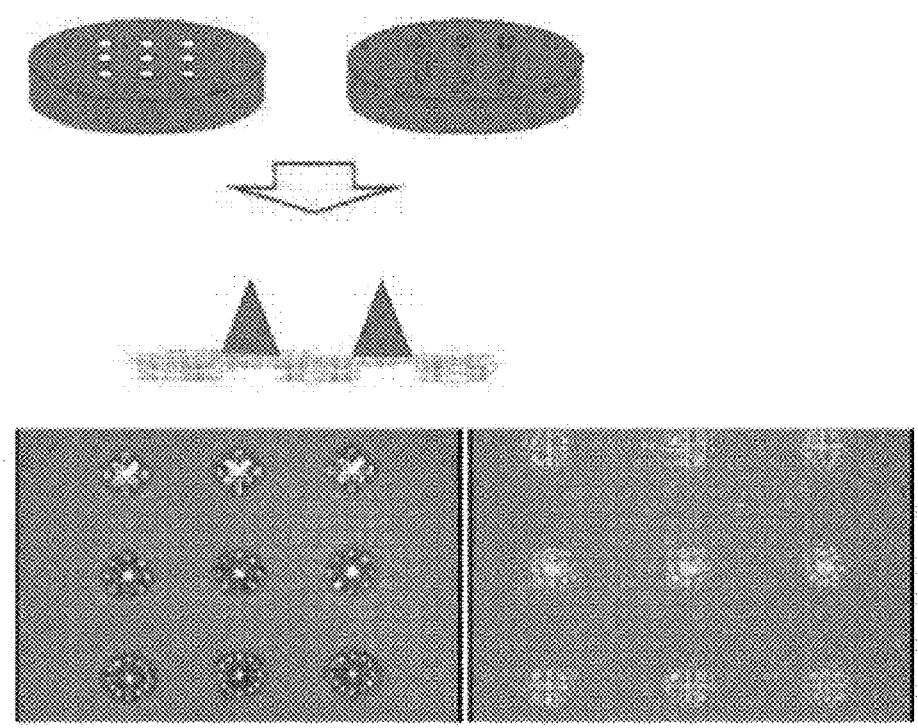
FIG. 6 shows an embodiment of the present invention with respect to a method for forming a pattern of a microporous structure.
Figure 7:
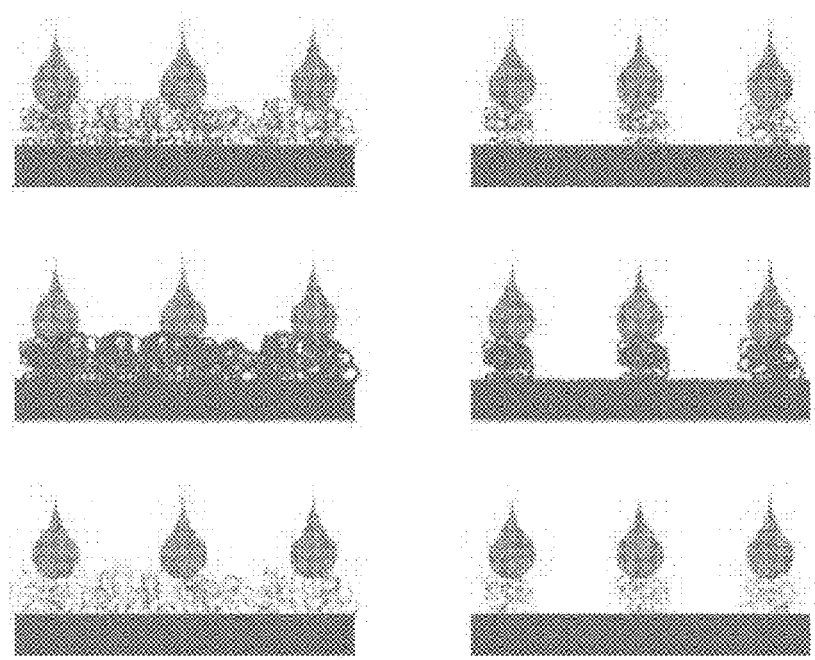
FIG. 7 shows detachable microstructures of the present invention for different concentrations (or frequencies) of the microporous structure, by which the hardness of the microporous structure can be controlled. The force and characteristics for detaching the microstructure can be controlled through the control of the hardness of the microporous structure.

According to an embodiment of the present invention, the microporous structure layer is patterned (see FIGS. 4 and 6). According to an embodiment of the present invention, the substrate is patterned (see FIGS. 4 and 5). The microstructure may be detached in various manners by controlling the pattern type of the microporous structure layer and/or the substrate.

According to an embodiment of the present invention, the substrate is patterned to have a pillar shape, and the microstructure is formed on the protrusion-shaped pillar of the microporous structure layer (see FIGS. 5A to 5D). Referring to FIGS. 5A to 5D, when a microneedle formed on the protrusion-shaped pillar of the substrate is inserted into the skin, the microporous structure layer receives force, and thus a weak area of the microporous structure layer is broken. Eventually, the microneedle is detached from the entire structure. FIGS. 5A to 5D show that the microporous structure layer is formed on the substrate which is patterned to have a pillar shape, and a weak area of the microporous structure layer is inclined from the protrusion of the substrate to the bottom of the substrate.

The manner, in which the substrate is manufactured, and the manner, in which the polymer solution (e.g., viscous composition) for forming a microporous structure layer is applied to the substrate, may be variously performed. According to an embodiment, the substrate or microporous structure layer is patterned, thereby preventing the loss of a drug loaded in the microstructure formed on the microporous structure layer, as much as possible. A representative embodiment will be described as follows:

According to a first embodiment, the substrate is physically patterned by forming grooves at predetermined intervals in a substrate. In such a case, a microporous structure layer is formed in the physically patterned region, and a viscous composition containing a drug is coated or dropped on the microporous structure layer. Here, in the procedure where the shape of the viscous composition is changed at the time of forming a microstructure, the amount of the viscous composition is minimized in the region other than the patterned region, thereby reducing the loss of the drug (see FIG. 6).

According to a second embodiment, the substrate is designed to be patterned into a hydrophilic region and a hydrophobic region. In such as case, the polymer composition used in the forming of the microporous structure layer is coated or dropped on an easily attachable region of the substrate depending on hydrophobic or hydrophilic characteristics of the polymer composition. For example, the hydrophilic polymer composition is mainly coated or dropped on the hydrophilic region of the substrate. In addition, even when the polymer composition is entirely coated or dropped on the substrate, the loss of the drug loaded in the microstructure can be reduced using a feature in which the polymer composition can gather in the easily attachable region of the substrate.

According to a third embodiment, both the first embodiment and the second embodiment are employed. In such a case, since the substrate has physically formed grooves, the substrate may be ready to pattern a polymer composition used to form a microporous structure layer, and the polymer composition can gather in the patterned region due to the gravity effect or chemical features of the hydrophilic or hydrophobic polymer composition even when the polymer composition is entirely coated or dropped.

According to an embodiment of the present invention, the substrate is a flat plate or a protrusion-shaped pillar. The protrusion-shaped pillar may be formed in various manners.

According to an embodiment of the present invention, the protrusion-shaped pillar may be formed by applying centrifugal force to a viscous composition (see FIG. 5G). For example, when the centrifugal force is applied to the viscous composition on a lower substrate, an upper substrate is positioned in the direction of the centrifugal force, and thus a pillar having a shape shown in FIG. 5G is formed. Then, the upper substrate is removed, thereby providing a plane on which the microstructure can be formed.

When the substrate used herein is a pillar, the microporous structure layer may be positioned in an upper, middle, or lower portion of the pillar (see FIG. 5H).

Figure 9:
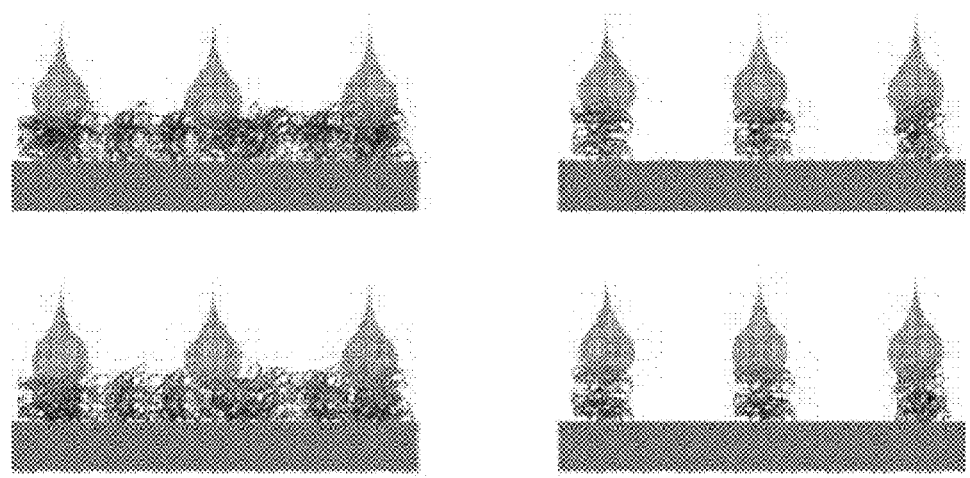
FIG. 9 shows multi-layered microporous structures. By differentiating chemical properties and/or physical properties of the microporous structure for different layers, the detachment point and the implantation function (detachment function) can be controlled.

According to an embodiment of the present invention, the microporous structure layer has multiple layers (see FIG. 9). In the multilayered microporous structure, the detachment function (or implantation function) of the microstructure can be controlled by differentiating chemical features and/or physical features of the respective layers.

Figure 12:
FIG. 12 shows embodiments in which microstructure-based drug delivery system was manufactured by diversifying the microporous structure layer. The microporous structure layer may be formed to have continuous microporous structures (lower images). In addition, the microporous structure layer may be formed to include a plurality of microporous structures that are distanced from each other two-dimensionally (upper images).

The microporous structure layer may be formed to have continuous microporous structures. In addition, the microporous structure layer may be formed to include a plurality of microporous structures that are distanced from each other two-dimensionally (see FIG. 12).

The microporous structure may selectively contain a drug.

The drug may be loaded in the microporous structure layer even after the microstructure is formed on the microporous structure layer. Alternately, the drug may be loaded in the microporous structure layer before the microstructure is formed. In addition, the drug may be loaded during the forming of the microporous structure layer. Thus, in the present invention, the time of loading a drug in the microporous structure layer should be widely construed. Most preferably, the loading of the drug is performed between steps (a) and (b).

Examples of the loading method of the drug in micropores include loading through simple contact, loading using contact and vibration, coating and loading using electric spray, loading using spray, and loading using solvent and then removing the solvent (Henry R Costantino, et al., Protein Spray-Freeze Drying. Effect of Atomization Conditions on Particle Size and Stability, Pharmaceutical Research, 17(11): 1374-1382 (2000)).

The drug that can be loaded herein is not limited, and thus may include liquid-phase or solid-phase drugs, and more specifically, a solid-phase drug.

The present invention is suitable for, particularly, the solid-phase drug. The solid-phase drug, e.g., powder drug is more stable than the liquid-phase drug, and thus the loading method of solid-phase drug using a microporous structure does not include a step of preparing a drug in a solution type. This can maintain the structure of the drug to be stable, and facilitate the delivery, storage, and distribution of sensitive drugs.

In addition, the method of loading a solid-phase drug in the microporous structure does not include a step of dissolving the drug in a separate solvent, and thus is very useful in delivering an insoluble drug in the body. Further, since a solvent harmful to the body is not used, the drug delivery can be stable.

The kind of drug loaded in the microporous structure layer will be described with reference to drugs contained in the microstructure as described below.

Figure 13:
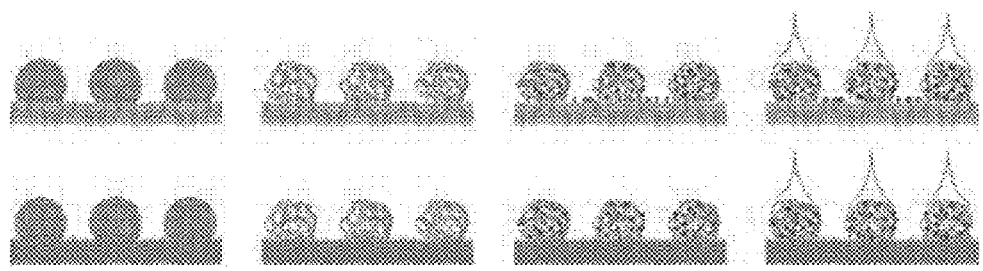
FIG. 13 shows that the attachment of the loaded drug to a support is controlled by controlling the surface characteristics of the support (substrate). A red support has surface characteristics onto which the drug is easily attached, and thus the drug is also attached to the support. However, a green support shown below has surface characteristics onto which the drug cannot be attached, and thus the drug is not present on a surface of the support. These surface characteristics of the support (substrate) may be variously controlled depending on the drug. The surface characteristics of the support can be variously controlled in consideration of hydrophobicity/hydrophilicity, electrostatic attraction, and/or chemical interaction.

According to an embodiment of the present invention, the attachment of the loaded drug to a support (substrate) can be controlled by controlling surface characteristics of the support. For example, referring to FIG. 13. a support shown on the top row has surface characteristics onto which the drug is easily attached, and thus the drug is also attached to the support. Meanwhile, a support shown on the bottom row has surface characteristics onto which the drug cannot be attached, and thus the drug is not present on a surface of the support. These surface characteristics of the support (substrate) may be variously controlled depending on the drug. In addition, the surface characteristics of the support can be variously controlled in consideration of hydrophobicity/hydrophilicity, electrostatic attraction, and/or chemical interaction.

Figure 14:
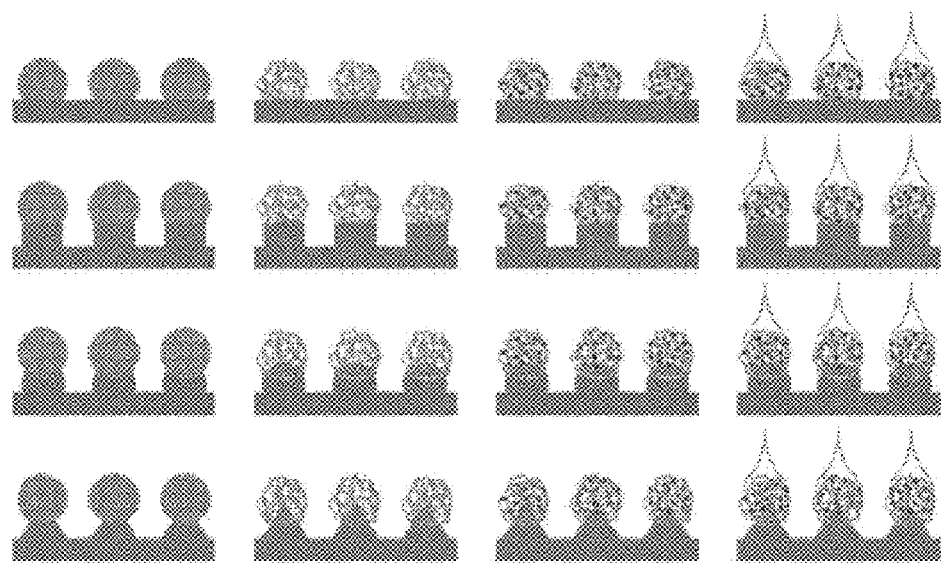
FIG. 14 shows embodiments in which the microstructure-based drug delivery systems were manufactured by diversifying the shape of the support (substrate).
Figure 15:
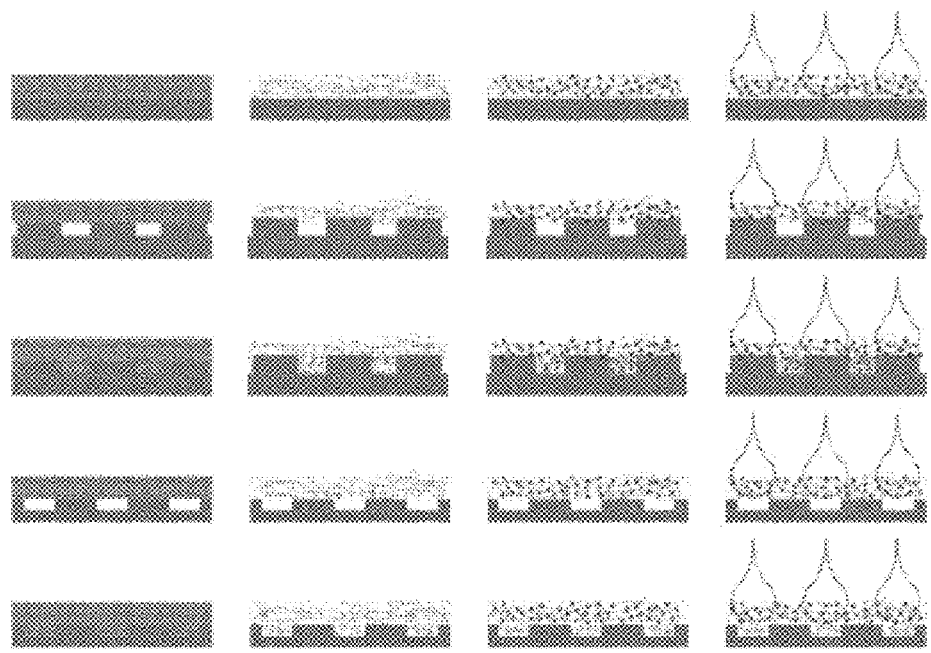
FIG. 15 shows embodiments in which microstructure-based drug delivery systems were manufactured using a microporous structure layer having continuous microporous structures, and various structures of supports (substrates).

According to an embodiment of the present invention, the shape of the support (substrate) may be verified when the microstructure-based drug delivery system is manufactured (see FIGS. 14 and 15). Various shapes of supports may influence the loading degree of drug, and the drug delivery control when applied to the skin.

According to an embodiment of the present invention, the loading amount of the drug is controlled by controlling the porosity of the microporous structure. The higher the porosity of the microporous structure, the more the drug (e.g., solid-phase drug) that can be loaded (see FIG. 16).

According to an embodiment of the present invention, the material constituting the microporous structure may be verified when a microstructure-based drug delivery system is manufactured. As can be seen in FIG. 17, two or more kinds of materials may be mixed to form a microporous structure, thereby controlling the size and frequency of micropores, porosity, electrostatic characteristics, and chemical or physical characteristics of the microporous structure layer.

In cases where the microporous structure layer has a plurality of layers, the drug loading characteristics can be controlled by controlling the features of the plurality of layers. For example, in the multi-layered microporous structure layer, respective layers may be the same or different, and the drug delivery characteristics can be controlled by controlling the physical, chemical, and electrical features of the respective layers (see FIG. 18A). In the multi-layered microporous structure layer, different kinds of drugs may be sequentially loaded in the layers, respectively (see FIG. 18B).

The drug loading may be performed in various manners. As can be seen in FIG. 19, the same kind of or two or more kinds of drugs may be loaded in one microporous structure. In addition, different kinds of drugs may be loaded in respective layers of the microporous structure layer having a multilayered structure, using characteristics of the microporous structure. The different kinds of drugs may be loaded sequentially or simultaneously.

According to an embodiment of the present invention, a protective layer is formed on the drug-loaded microporous structure layer to prevent the loss of the drugs. The protective layer may be formed in order to prevent the loss of the drug due to the external environment after the drug is loaded in the microporous structure. In addition, a component of the microneedle itself is used as a protectable component, thereby providing a protection function to the microneedle.

(b) Forming of Microstructure

The microstructure is formed on the microporous structure layer.

The microstructure may be formed using a viscous composition. As used herein, the term "viscous composition" refers to any composition that can be shape-transformed to form a microstructure.

The viscosity of the viscous material may be variously changed depending on kinds, concentrations, or temperatures of materials contained in the composition or by adding a viscosity modifying agent or the like, and may be appropriately adjusted to suit the purpose of the present invention. The viscosity of the viscous composition may be adjusted by the inherent viscosity of a viscous material, and may be adjusted by further adding a viscosity modifying agent to the viscous composition.

For example, a viscosity modifying agent that is conventionally used in the art, such as hyaluronic acid or a salt thereof, polyvinyl pyrrolidone, a cellulosic polymer, dextran, gelatin, glycerin, polyethylene glycol, polysorbate, propylene glycol, povidone, carbomer, ghatti gum, guar gum, glucomannan, glucosamine, dammer resin, rennet casein, locust bean gum, microfibrillated cellulose, psyllium seed gum, xanthan gum, arabino galactan, Arabic gum, alginates, gelatin, gellan gum, carrageenan, karaya gum, curdlan, chitosan, chitin, tara gum, tamarind gum, tragacanth gum, furcelleran, pectin, or pullulan, may be added to a main ingredient of the microstructure, e.g., a composition containing a biocompatible composition, may be added to the viscous composition, thereby adjusting the viscosity of the composition to suit the purpose of the present invention. Preferably, the viscous composition used herein exhibits viscosity of 200,000 cSt or lower.

According to an embodiment of the present invention, the viscous composition used herein contains a biocompatible or biodegradable composition. As used herein, the term "biocompatible material" refers to any material that is substantially non-toxic to the human body, chemically inactive, and has no immunogenicity. As used herein, the term "biodegradable material" refers to a material that is in vivo biodegradable by body fluids or microorganisms.

According to an embodiment of the present invention, a viscous composition includes hyaluronic acid and its salts, polyvinylpyrrolidone, cellulose polymer (for example, hydroxypropyl methylcellulose, hydroxyalkyl cellulose, hydroxyethyl cellulose, hydroxypropyl cellulose, ethyl hydroxyethyl cellulose, alkyl cellulose and carboxymethyl cellulose), dextran, gelatin, glycerin, polyethyleneglycol, polysorbate, propyleneglycol, povidone, carbomer, gum ghatti, guar gum, glucomanan, glucosamine, dammer resin, rennet casein, locust bean gum, microfibrillated cellulose, psyllium seed gum, xanthan gum, arabino galactan, arabic gum, alginic acid, gelatin, gellan gum, carrageenan, karaya gum, curdlan, chitosan, chitin, tara gum, tamarind gum, tragacanth gum, furcelleran, pectin and pullulan.

Optionally, the viscous composition may contain a biocompatible and/or biodegradable material as a main component.

The biocompatible and/or biodegradable materials include polyester, PHAs, poly(a-hydroxy acid, poly(β-hydroxy acid, poly(3-hydroxybutyrate-co-valerate; PHBV), poly(3-hydroxyproprionate; PHP), poly(3-hydroxyhexanoate; PHH), poly(4-hydroxy acid), poly(4-hydroxybutyrate), poly(4-hydroxy valerate), poly(4-hydroxyhexanoate), poly (esteramide), polycarprolactone, polylactide, polyglycoride, poly(lactide-co-glycoride; PLGA), polydioxanone, polyorthoester, polyetherester, polyanhydride, poly(glycolacid-co-trimethylene carbonate), polyphosphoester, polyphosphoester urethane, poly(amino acid), polycyanoacrylate, poly(trimethylene carbonate), poly(iminocarbonate), poly (tyrosine carbonate), polycarbonate, poly(tyrosine arylate), polyalkylene oxalate, polyphosphagens, PHA-PEG, ethylene vinyl alcohol copolymer (EVOH), polyurethane, silicon, polyester, polyolefin, polyisobutylene, ethylene-alphaolefin copolymer, stylene-isobtylene-stylene triblock copolymer, acryl polymer and copolymer, vinyl halide polymer and copolymer, polyvinyl chloride, polyvinyl ether, polyvinyl methly ether, polyvinyliden halide, polyvinyliden fluoride, polyvinyliden chloride, polyfluoroalkene, polyfluoroalkene, polyacrylonitrile, polyvinyl ketone, polyvinyl aromatics, polystylene, polyvinyl ester, polyvinyl acetate, ethylenemethly metacrylate copolymer, acrylonitrile-stylene copolymer, ABS resin and ethylene-vinyl acetate copolymer, polyamide, alkyid resin, polyoxymethylene, polyimide, polyether, polyacrylate, polymetacrylate, polyacrylate-co-malic acid, chitosan, dextran, cellulose, heparin, hyaluronic acid, alginate, inulin, starch or glycogen, preferably polyester, polyhydroxyalkanoate (PHAs), poly(a-hydroxy acid), poly(β-hydroxy acid), poly(3-hydroxybutylate-co-valerate; PHBV), poly(3-hydroxyproprionate; PHP), poly(3-hydroxyhexanoate; PHH), poly(4-hydroxy acid), poly(4-hydroxybutylate), poly(4-hydroxy valerate), poly(4-hydroxyhexanoate), poly(esteramide), polycarprolactone, polylactide, polyglycoride, poly(lactide-co-glycoride; PLGA), polydioxanone, polyorthoester, polyetherester, polyanhydride, poly(glycolic acid-co-trimethylene carbonate), polyphosphoester, polyphosphoester urethane, poly(amino acid), polycyanoacrylate, poly(trimethylene carbonate), poly(iminocarbonate), poly(tyrosine carbonate), polycarbonate, poly(tyrosine arylate), polyalkylene oxalate, polyphosphagens, PHA-PEG, chitosan, dextran, cellulose, heparin, hyaluronic acid, alginate, inulin, starch and glycogen.

According to an embodiment of the present invention, the viscous composition used herein is dissolved in an appropriate solvent to exhibit viscosity. Meanwhile, some of the materials exhibiting viscosity may exhibit viscosity when melted by heat. In order to maximize one of the advantages of the present invention, such as a non-heating process, a material used as the viscous composition exhibits viscosity when dissolved in an appropriate solvent.

The solvent which is used to prepare the viscous composition by dissolving a viscous material is not particularly limited, and water, anhydrous or hydrous lower alcohols having 1 to 4 carbon atoms, acetone, ethyl acetate, chloroform, 1,3-butylene glycol, hexane, diethyl ether, or butyl acetate may be used as the solvent.

According to an embodiment of the present invention, the viscous material further contains a drug. A microneedle is one of main uses of the microstructure of the present invention, and is used for the purpose of transdermal administration. Therefore, the drug is added to the biocompatible material during the preparing procedure of the viscous composition.

The drug that can be used herein is not particularly limited. For example, the drug includes chemical drugs, protein medicines, peptide medicines, nucleic acid molecules for gene therapy, nanoparticles, and active ingredients and cosmetic ingredients for functional cosmetics.

Examples of the drug usable herein may include anti-inflammatory agents, pain relievers, anti-arthritic agents, antispasmodics, anti-depressive agents, antipsychotics, tranquilizers, anti-anxiety drug, narcotic antagonists, anti-Parkinson's disease drugs, cholinergic agonists, anti-cancers, anti-angiogenic agents, immunosuppressive agents, antiviral agents, antibiotics, appetite suppressants, pain relievers, anti-cholinergic agents, anti-histamines, anti-migraine agents, hormonal agents, coronary, cerebral or peripheral vasodilators, contraceptives, anti-thrombotic agents, diuretics, antihypertensive agents, cardiovascular therapeutic agents, and cosmetic ingredients (e.g., anti-wrinkle agent, skin aging inhibitor, and skin whitening agent), but are not limited thereto.

According to an embodiment of the present invention, the microstructure according to the present invention is manufactured under non-heating treatment conditions or at room temperature or at a low temperature lower than the room temperature (e.g., 5 to 20). Therefore, according to the present invention, even when the drug used herein is a heat-sensitive material, such as a protein medicine, a peptide medicine, or a nucleic acid molecule for gene therapy, it is possible to manufacture a microstructure involving the drug.

According to an embodiment of the present invention, the method of the present invention is used to manufacture a microstructure involving a heat-sensitive drug, for example, a protein medicine, a peptide medicine, or vitamin (preferably, vitamin C).

The protein/peptide medicine involved in the microstructure by the method of the present invention is not particularly limited, and examples thereof may include hormones, hormone analogues, enzymes, enzyme inhibitors, signaling proteins or fragments thereof, antibodies or fragments thereof, single chain antibodies, binding proteins or binding domains thereof, antigens, adhering proteins, structural proteins, regulatory proteins, toxin proteins, cytokines, transcription factors, blood coagulation factors, and vaccines, but are not limited thereto. In more detail, the protein/peptide drugs include insulin, IGF-1 (insulin-like growth factor 1), growth hormone, erythropoietin, G-CSFs (granulocyte-colony stimulating factors), GM-CSFs (granulocyte/macrophage-colony stimulating factors), interferon alpha, interferon beta, interferon gamma, interlukin-1 alpha and beta, interlukin-3, interlukin-4, interlukin-6, interlukin-2, EGFs (epidermal growth factors), calcitonin, ACTH (adrenocorticotropic hormone), TNF (tumor necrosis factor), atobisban, buserelin, cetrorelix, deslorelin, desmopressin, dynorphin A (1-13), elcatonin, eleidosin, eptifibatide, GHRH-II (growth hormone releasing hormone-II), gonadorelin, goserelin, histrelin, leuprorelin, lypressin, octreotide, oxytocin, pitressin, secretin, sincalide, terlipressin, thymopentin, thymosine α1, triptorelin, bivalirudin, carbetocin, cyclosporin, exedine, lanreotide, LHRH (luteinizing hormone-releasing hormone), nafarelin, parathyroid hormone, pramlintide, T-20 (enfuvirtide), thymalfasin and ziconotide.

According to an embodiment of the present invention, the viscous material further includes energy. In this case, the microstructure may be used to transfer or deliver energy, such as heat energy, light energy, or electrical energy. For example, with respect to photodynamic therapy, the microstructure may be used to induce light to a specific site of the human body, so that the light can be applied directly to tissues or the light can be applied to intermediates such as light-sensitive molecules.

According to an embodiment of the present invention, the viscous composition is placed in a drop form on the microporous structure layer. That is, the viscous composition may be dropped in a drop form on the microporous structure layer. According to another embodiment, the viscous composition may be coated on the microporous structure layer.

The microstructure may be formed in various manners. Exemplary methods for forming the microstructure are as follows:

First, the microstructure may be formed following the method disclosed in Korean Patent Registration No. 0793615 and developed by the present inventors. For example, the microstructure may be formed by coating or dropping a viscous composition on the microporous structure layer, solidifying the viscous composition while drawing the viscous composition using a contact protrusion of a lifting support, and then cutting the drawn viscous composition.

Second, the microstructure may be formed following the method disclosed in Korean Patent Registration No. 1136738 and developed by the present inventors. For example, the microstructure may be formed by coating or dropping a viscous composition on the microporous structure layer, contacting a contact protrusion of a lifting support with the viscous composition, and then ventilating the viscous composition.

Third, the microstructure may be formed following the method disclosed in Korean Patent Application No. 2013-0019247 and developed by the present inventors. For example, the microstructure may be formed by dropping a viscous composition on the microporous structure layer, and then applying a negative pressure to the dropped spot.

Fourth, the microstructure may be formed following the method disclosed in Korean Patent Application No. 2013-0050462 and developed by the present inventors. For example, the microstructure may be formed by dropping a viscous composition on the microporous structure layer, and then applying centrifugal force to the dropped spot.

Fifth, the microstructure may be formed by contacting a viscous composition spot dropped on a lifting support with the microporous structure layer, and then upwardly moving the lifting support.

Sixth, the microstructure is formed on the microporous structure layer by positioning a lifting support including a viscous composition spot on the microporous structure layer, and then applying centrifugal force to the spot to draw the spot.

The foregoing methods for forming the microstructure are illustrated as examples. In cases where a heat-sensitive drug is loaded in the microneedle, it is preferable to form the microstructure as the third, fourth, and sixth exemplary methods.

The present invention can provide various microstructures, and for example, a microneedle, microblade, microknife, microfiber, microspike, microprobe, microbarb, microarray, or microelectrode may be provided.

According to an embodiment of the present invention, the microstructure is detachable from the microporous structure.

According to an embodiment of the present invention, the microstructure-based drug delivery system is manufactured by controlling the size and shape of the microneedle on the microporous structure layer. Various shapes and sizes of microneedles may be formed on the microporous structure layer, and through these, drug release characteristics, drug skin permeability, and the like can be controlled. In addition, a microneedle covering the microporous structure serves to protect the microporous structure.

According to an embodiment of the present invention using a pillar support, the method of the present invention includes the following steps of: (i) applying centrifugal force to a viscous composition on a lower substrate to prepare a pillar support, wherein an upper plate is positioned in a direction of the centrifugal force; (ii) removing the upper plate, and then forming a microporous structure on the pillar support (e.g., the microporous structure is formed by discharging a polymer composition and performing freeze-drying, or through electrospinning); and (iii) forming a microstructure on the microporous structure. In such a case, the drug may be loaded in the microporous structure after the microporous structure is formed. Optionally, the drug may be contained in the microstructure on the microporous structure.

According to another embodiment of the present invention using a pillar support, the method of the present invention includes the following steps of (see FIG. 5B): (i) forming microporous structures on an array of pillar supports formed on a plate through electrospinning; and (ii) forming microstructures on the microporous structures. More specifically, the thus formed microporous structure includes a fiber dense area, which is formed on an upper portion of the pillar and has a relatively low occupation of micropores, and a fiber hung area, which is inclined from the top of the pillar to the bottom of the plate and has a relatively high occupation of micropores (see FIG. 5D). In such a case, the drug may be loaded in the microporous structure after the microporous structure is formed. Optionally, the drug may be contained in the microstructure on the microporous structure.

In accordance with another aspect of the present invention, there is provided a microstructure-based drug delivery system, including: (a) a microporous structure layer; and (b) a microstructure formed on the microporous structure layer, wherein at least one of the microporous structure layer and the microstructure contains a drug, and wherein the microstructure contains or does not contain a liquid-phase or solid-phase drug if the drug is loaded in the microporous structure layer.

According to an embodiment of the present invention, the microstructure of the present invention is detachable from the microporous structure.

According to an embodiment of the present invention, the microstructure-based drug delivery system of the present invention further includes a substrate supporting a microporous structure layer. According to an embodiment of the present invention, the substrate is a flat plate or a protrusion-shaped pillar.

According to an embodiment of the present invention, the microstructure-based drug delivery system of the present invention is formed by the method of the present invention.

According to an embodiment of the present invention, the microporous structure layer is formed on the protrusion-shaped pillar, and the microstructure is formed on the microporous structure layer. More specifically, the microporous structure formed on the protrusion-shaped pillar includes a fiber dense area, which is formed on an upper portion of the pillar and has a relatively low number of micropores, and a fiber hung area, which is inclined from the top of the pillar to the bottom of the plate and has a relatively high number of micropores (see FIG. 5d). When the microstructure-based drug delivery system of the present invention is applied to the skin, the fiber hung area is broken, resulting in the detachment of the microstructure.

The drug delivery system of the present invention can be used as various drug delivery systems, and for example, may be manufactured and used as a transdermal drug delivery system, a balloon type drug delivery system, and a stent type drug delivery system.

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1: Microporous Structure Forming I

A microporous structure was formed using electrospinning. More specifically, a corresponding solution is put in a 50 mL syringe, and then electrospun through a stainless steel needle at a high voltage of 9 kV. An aluminum substrate is positioned 90 mm below a spray port, and then electrospinning was performed.

Figure 2A:
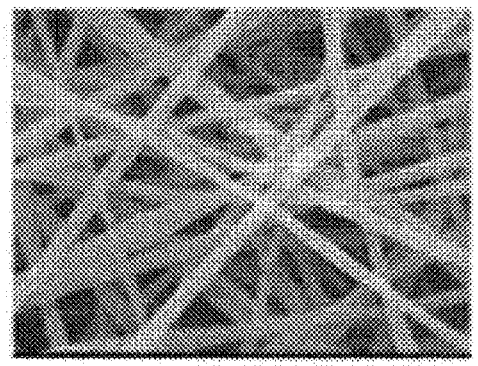
FIGS. 2A to 2F show images illustrating microporous structures formed using electrospinning.
Figure 2B:
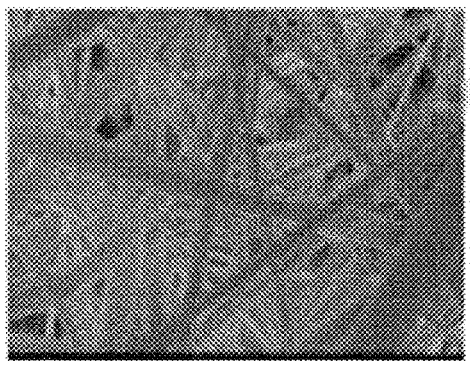
Figure 2C:
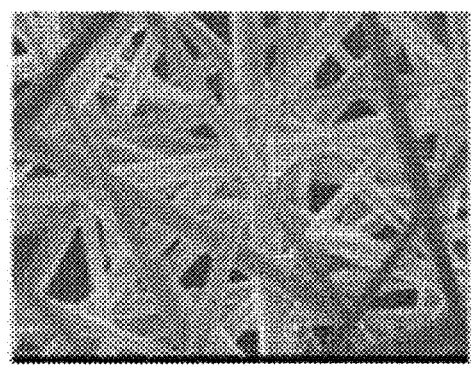
Figure 2D:
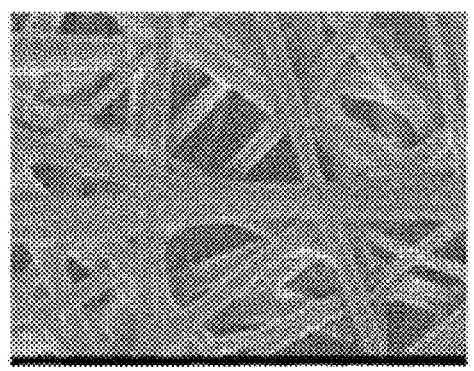
Figure 2E:
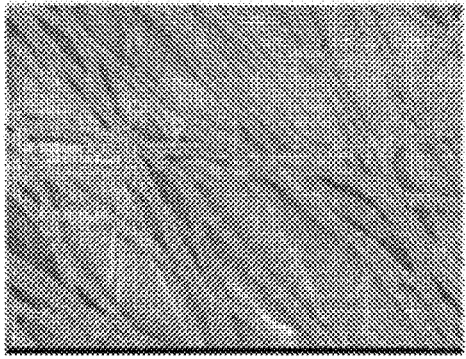
Figure 2F:
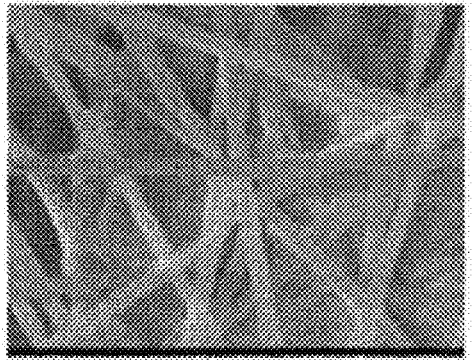

Referring to FIGS. 2A to 2E, FIG. 2A shows a surface observation result of a microporous structure formed by electrospinning a 15% polyvinyl alcohol (PVA) solution (×50,000 magnification). FIG. 2B shows a surface observation result of a microporous structure formed by electrospinning an 8% polyvinylpyrrolidone (PVP) solution (×7,000 magnification). FIG. 2C shows a surface observation result of a microporous structure formed by electrospinning a 5% polyethylene oxide (PEO) solution (×7,000 magnification). FIG. 2D shows a surface observation result of a microporous structure formed by electrospinning a 15% poly(lactic-co-glycolic) acid (PLGA) solution (×7,000 magnification). FIG. 2E shows a surface observation result of a microporous structure formed by electrospinning an 11% polyurethane (PU) solution (×7,000 magnification). FIG. 2F shows a surface observation result of a microporous structure formed by electrospinning a 10% polycaprolactone (PCL) solution (×50,000 magnification). As can be confirmed in FIGS. 2A to 2F, the microporous structure layers exhibiting various porosities depending on the kind of polymer used were formed.

Example 2: Microporous Structure Forming II and Drug Loading

A microporous structure was formed using freeze-drying. More specifically, 50 µg of a 10% (w/v) solution of carboxymethyl cellulose (CMC, Sigma-Aldrich) was dropped on an aluminum substrate, frozen using liquefied nitrogen, and then freeze-dried at −80° C. for 200 minutes using a freeze-drier, thereby forming a microporous structure (see FIG. 3).

Figure 3A:
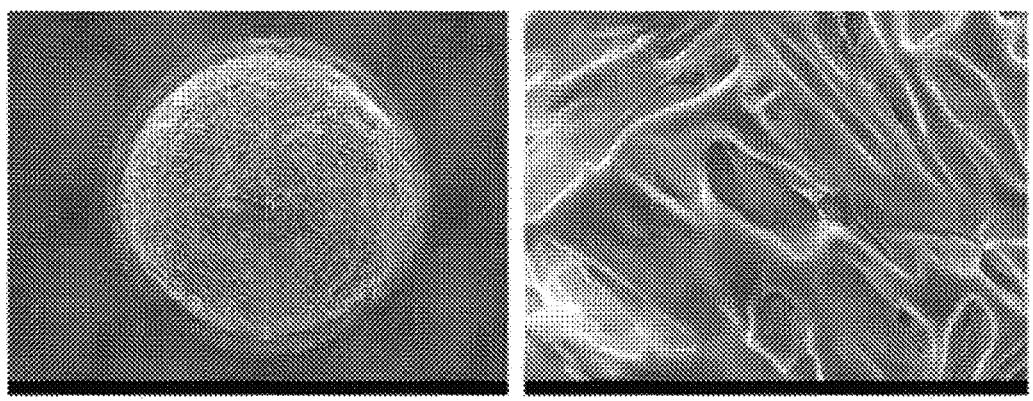
FIG. 3A shows images illustrating a microporous structure formed using freeze-drying.

As can be confirmed in FIG. 3A, the polymer (CMC) solution was discharged and then freeze-dried, thereby forming a microporous structure with a semi-spherical shape. In FIG. 3, the left panel shows an image obtained by magnifying a surface of a microporous structure at a magnification of .times.85, and the right panel shows an image obtained by magnifying the same at a magnification of ×1000, indicating the formation of micropores.

Figure 3B:
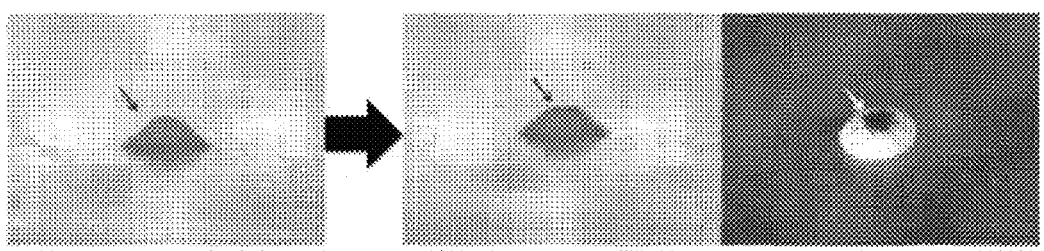
FIG. 3B shows that a solid powder material (Rhodamine B) was loaded in the microporous structure through vibration (left panel: before loading, right panel: after loading). It could be confirmed that a solid powder material (indicated by each arrow) exhibiting a red color is loaded in the microporous structure through contact and vibration.

FIG. 3B shows that a solid powder material (Rhodamine B) was loaded in the microporous structure through vibration (left panel: before loading, right panel: after loading). It could be confirmed that a solid powder material exhibiting a red color is loaded in the microporous structure through contact and vibration.

Example 3: Microporous Structure Forming III

A microporous structure was formed on a support having a convex portion (i.e., a protrusion-shaped pillar) using electrospinning. An electrospinning device is composed of an injection pump, a high-voltage power supply, and a grounded target. More specifically, a CMC 10% (w/v) solution was put in a 5 mL plastic syringe, and was injected at an injection rate of 3 mL/h using the injection pump. A high voltage of 9 kV was applied to the CMC solution to perform electrospinning. A microporous structure was formed in a net-like shape on a pillar-shaped support (support having a convex portion).

As can be confirmed in FIGS. 5B and 5C, the microporous structure was successfully formed on the pillar-shaped support by electrospinning. In addition, a weak area of the microporous structure layer was inclined from a protrusion of the substrate to the bottom of the substrate. In FIG. 5C, panels A to D show observation results at magnifications of ×20, ×40, ×10, and ×40, respectively.

FIG. 5D shows field emission scanning electron microscopy (FESEM) images of FIG. 5C. As can be seen from FIG. 5D, it was confirmed that different fabric structures of micropores were formed for respective areas. It was confirmed that a fiber hung area which is called because it has a relatively fiber density and thus a great percentage of micropores was broken, and thus the detachment of the microstructure occurred. In the lower images of FIG. 5d, the 100, 300, and 500 μm indicate heights at different regions of the pillar, and it was confirmed that the higher portion of the pillar had a higher percentage of micropores, and thus the detachment of the microstructure occurred more easily.

Example 4: Microporous Structure Forming IV

First, a pillar as a support was formed by applying centrifugal force to a hyaluronic add solution (30 kDa, 60% (w/v)), which was used as a raw material, according to the method (Korean Patent Application No. 2013-0050462) developed by the present inventors (see FIG. 5E). A hyaluronic acid solution (150 kDa, 2% (w/v)) was discharged on the pillar, which was then immersed in liquefied nitrogen to be frozen, and then subjected to freeze-drying, thereby forming a microporous structure.

As can be seen from FIG. 5F, the microporous structure was formed on the pillar. A solid powder type drug was loaded using the same to form a microneedle structure, thereby delivering the drug into the skin.

Example 5: Microporous Structure Patterning

A microporous structure was designed to have predetermined patterns. More specifically, as shown in the left image of the upper part of FIG. 6, an aluminum substrate having holes with a predetermined shape was prepared. Then, microporous structures were formed on the substrate through electrospinning by the same method as in example 3.

As can be confirmed in FIG. 6, microporous structures having predetermined patterns were formed.

Example 6: Manufacturing of Microstructure-Based Drug Delivery System

A microstructure-based drug delivery system of the present invention was manufactured. More specifically, a microporous structure was formed on a pillar-shaped support using electrospinning by the same method as in example 3. As a viscous composition for form a microneedle, hyaluronic acid (Soliance) was used. 8,000 mg of hyaluronic acid (molecular weight: 29 kDa) was dissolved in 20 ml of deionized distilled water to prepare a 40% (w/v) solution. A viscous solution drop of the 40% hyaluronic acid was formed on the formed microporous structure, and subjected to drawing using a lifting support having a contact protrusion, thereby forming a microneedle on the microporous structure.

Figure 8:
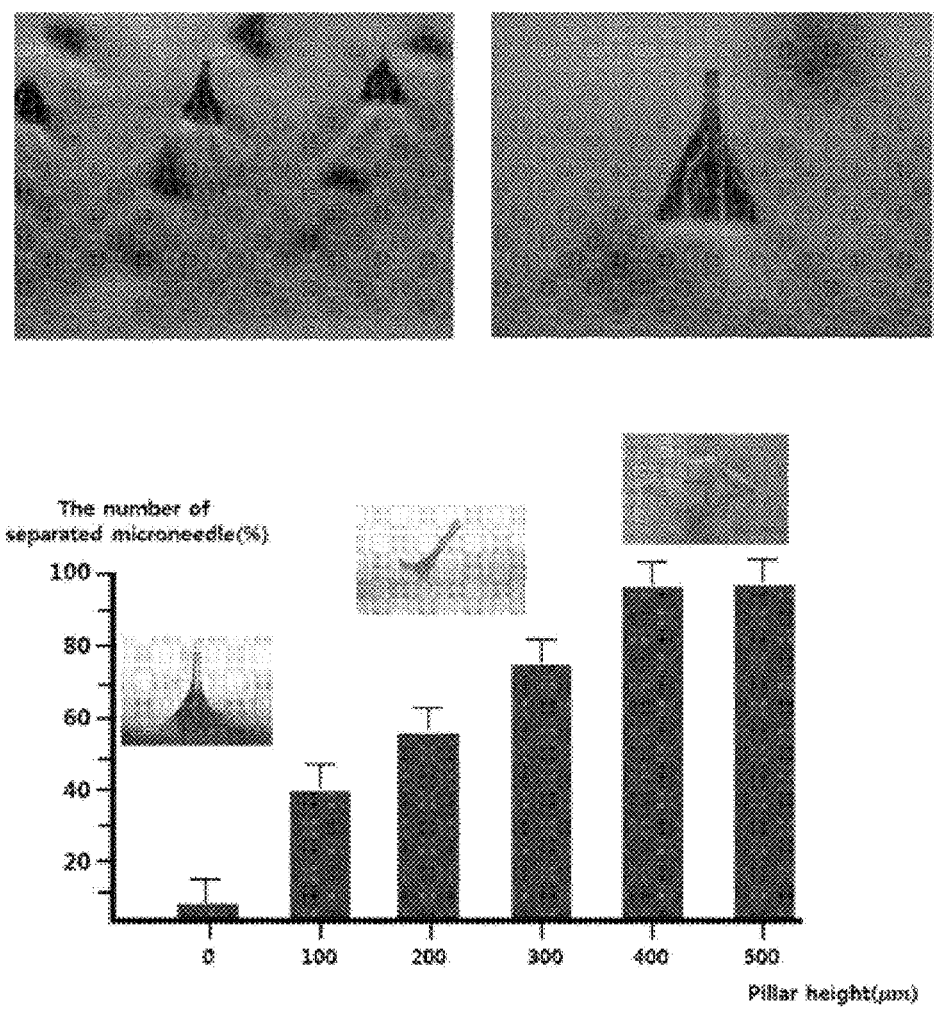
FIG. 8 shows results of forming a microneedle on a microporous structure.

As can be seen in FIG. 8, a microneedle was formed on the microporous structure (upper image). In addition, the larger the pillar height, the higher the degree of the microneedle detached (lower image).

Example 7: Application of Microstructure-Based Drug Delivery System

Figure 10A:
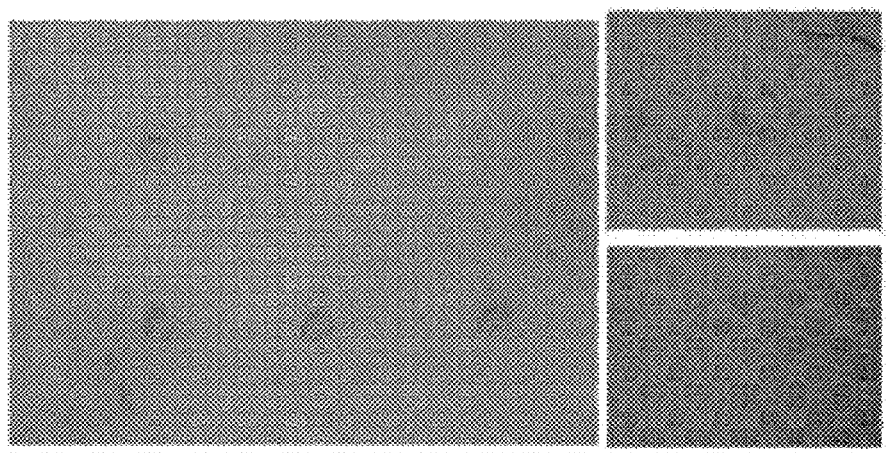
FIGS. 10A and 10B show results of applying the detachable microstructure to the skin. It was confirmed that the microporous structure on the support was broken, and thus the microneedles were detached, and then implanted in the skin. Green regions indicate microneedles, and white regions indicate a microporous structure formed using electrospinning.
Figure 10B:
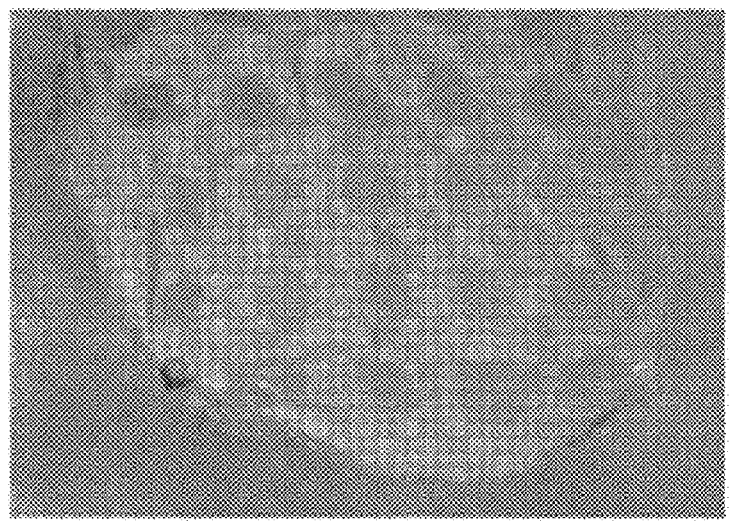

The microstructure-based drug delivery system of the present invention was applied to the skin. A detachable microstructure used herein was formed according to example 5. The thus formed detachable microstructure was applied to the human skin. It was confirmed from FIG. 10A that the microporous structure on the support was broken, and the microneedle was detached and then implanted in the skin. FIG. 10B shows the micropores structure after the microneedles were detached.

It was therefore confirmed that the detachable microstructure of the present invention is applied to human skin, and then effectively detached from the support, thereby delivering a drug into the skin.

Example 8: Application of Microstructure-Based Drug Delivery System

Figure 11A:
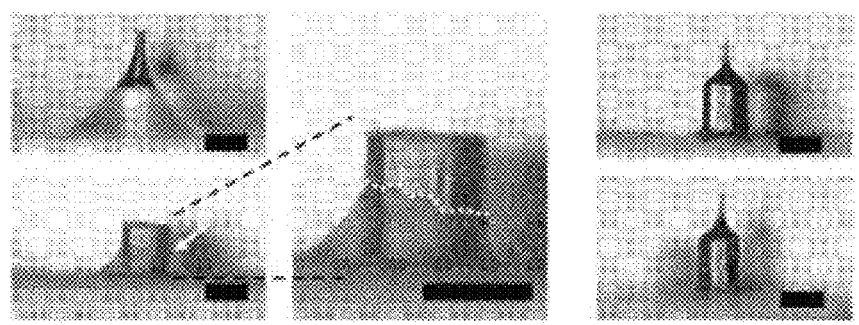
FIG. 11A shows images illustrating that a microporous structure was formed on the pillar support through electrospinning by the same method as in example 6, and a red microneedle was formed thereon.
Figure 11B:
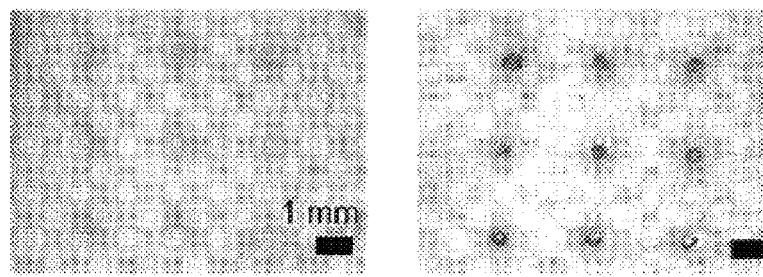
FIG. 11B shows images illustrating results of applying the microstructure-based drug delivery system of FIG. 11A to the human skin.

A microporous structure was formed on the pillar support through electrospinning by the same method as in example 6, and a red microneedle was formed thereon (FIG. 11A). The thus manufactured microstructure-based drug delivery system was applied to the human skin. It was confirmed from FIG. 11A that, as indicated by an arrow and a dot line, the microporous structure was torn out, and the microneedle was detached from the pillar and embedded in the skin. Whereas, it was confirmed that, in cases where the microporous structure was not present as shown in the right panel, the microneedle remained intact on the pillar, without being detached and embedded, even after the application to the skin. FIG. 11B shows images illustrating results of applying the microstructure-based drug delivery system to human skin. The left panel shows a result of applying microneedles without being detached due to the absence of the microporous structure. There are no red microneedles but scars of application of the red microneedles. Whereas, the right panel shows that red microneedles are detached and implanted in the skin as a result of applying the microneedles when the microporous structure is present.

Figure 11C:
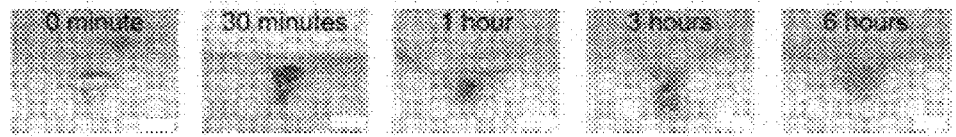
FIG. 11C shows images illustrating results of applying the microstructure-based drug delivery system of FIG. 11A to the human skin as time passes.

FIG. 11C shows images illustrating the result of applying the microstructure-based drug delivery system to the skin as time passes. When the microstructure-based drug delivery system of the present invention was applied, the microneedle was implanted in the skin due to the detaching function of the microporous structure, and then dissolved over time. The microneedle implanted in the skin was dissolve in water in the body at body temperature, leading to permeation into the skin.

Features and advantages of the present invention are summarized as follows:

(a) The present invention provides a microstructure-based drug delivery system which is physically detachable using a microporous structure layer.

(b) The present invention can skip a drying step which is essential for the manufacturing process of the existing biodegradable microneedle, and solve the problem in that the hardness of the microneedle is reduced when the microneedle contains drugs, failing to penetrate the skin.

(c) The microstructure of the present invention is implantable in the body through the insertion into the body and detachment from the microporous structure.

(c) The detachable microstructure of the present invention can be applied to wrinkled (skin movement) and corrugated parts through a detachment function thereof.

(d) According to the present invention, the detachable microstructure can remarkably overcome problems of the prior art, such as a feeling of irritation caused by a long application time, shrinkage of activity of a user, and the limitation of the applicable part, by minimizing the time of patch attachment (microneedle application), and thus, can promote convenience of the user or patient compliance.

(e) The present invention can overcome the problems of application of the existing patch, that is, the limitation of the applicable part due to properties of the patch, such as elasticity and adhesive strength, and skin elasticity, movement, and corrugation.

(f) The present invention is suitable for, particularly, a solid-phase drug. Since the solid-phase drug, e.g., powder drug is more stable than the liquid-phase drug, the loading method of solid-phase drug using a microporous structure does not include a step of preparing drug in a solution type. This can maintain the structure of drug to be stable, and facilitate the delivery, storage, and distribution of sensitive drug.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for manufacturing a microstructure-based drug delivery system using a microporous structure, the method comprising:
   (a) forming a microporous structure layer on a protrusion-shaped pillar of a substrate, wherein the microporous structure includes a fiber dense area formed on an upper portion of the pillar and a fiber hung area inclined from an apex of the protrusion to a perimeter around the protrusion that is greater than a perimeter of a base of the protrusion and does not overlap with another fiber hung area and the fiber hung area has more micropores than the fiber dense area;
   (b) forming a microstructure on the microporous structure layer, wherein the microstructure is formed using a viscous composition containing a liquid-phase or solid-phase drug if the drug is loaded in the microstructure; and
   (c) loading a liquid-phase or solid-phase drug in the microporous structure layer after step (a) or (b) if the drug is loaded in the microporous structure layer,
   wherein at least one of the microporous structure layer and the microstructure contains the drug.

2. The method of claim 1, wherein the microstructure is detachable from the substrate at the microporous structure.

3. The method of claim 2, wherein the substrate is patterned.

4. The method of claim 1, wherein the drug is loaded in the microporous structure layer by loading through contact, loading using contact and vibration, coating and loading using electric spray, loading using spraying, or loading using a solvent and then removing the solvent.

5. The method of claim 1, wherein the microporous structure layer of step (a) is formed by freeze-drying, electrospinning, or solvent removal.

6. The method of claim 5, wherein the microporous structure layer is formed by electrospinning, and the size and frequency of micropores of the microporous structure layer is controlled by controlling the thickness, diameter, or density of a polymer fiber generated by the electrospinning.

7. The method of claim 1, wherein the microporous structure layer is formed using a polymer solution, and the size and frequency of micropores, porosity, electrostatic properties, chemical properties, or physical properties of the microporous structure layer are controlled by controlling the kind, molecular weight, concentration, or a combination thereof of the polymer.

8. The method of claim 1, wherein the microstructure of step (b) is formed using a viscous composition.

9. The method of claim 8, wherein the viscous composition is placed in a drop shape on the microporous structure layer.

10. The method of claim 1, wherein a protective layer is formed on the drug-loaded microporous structure layer to prevent the loss of the drug.

11. The method of claim 1, wherein the microporous structure layer is patterned.

12. The method of claim 1, wherein the microporous structure layer has multiple layers.

13. A microstructure-based drug delivery system, comprising:
   (a) a microporous structure layer formed on a protrusion-shaped pillar of a substrate, wherein the microporous structure includes a fiber dense area formed on an upper portion of the pillar and a fiber hung area inclined from an apex of the protrusion to a perimeter around the protrusion that is greater than a perimeter of a base of the protrusion and does not overlap with another fiber hung area and the fiber hung area has more micropores than the fiber dense area; and
   (b) a microstructure formed on the microporous structure layer,
   wherein at least one of the microporous structure layer and the microstructure contains a drug.

14. The microstructure-based drug delivery system of claim 13, wherein the microstructure is detachable from the substrate at the microporous structure layer.

* * * * *